United States Patent [19]

Sairenji

[11] Patent Number: 4,725,265
[45] Date of Patent: Feb. 16, 1988

[54] SYRINGE

[75] Inventor: Michihiko Sairenji, Tokyo, Japan

[73] Assignee: Sairenji Trading Co., Ltd., Tokyo, Japan

[21] Appl. No.: 934,851

[22] Filed: Nov. 25, 1986

[30] Foreign Application Priority Data

Dec. 2, 1985 [JP] Japan .......................... 60-185904[U]

[51] Int. Cl.⁴ .............................................. A61M 5/00
[52] U.S. Cl. ..................................... 604/112; 604/113
[58] Field of Search ................ 604/112, 113; 128/399, 128/400, DIG. 27

[56] References Cited

U.S. PATENT DOCUMENTS 3,605,742 9/1971 Tibbs ................................... 604/112

FOREIGN PATENT DOCUMENTS 3203950 11/1983 Fed. Rep. of Germany ...... 604/113

Primary Examiner—John D. Yasko
Attorney, Agent, or Firm—Cushman, Darby & Cushman

[57] ABSTRACT

Disclosed is a syringe which comprises a cylindrical hollow member having its forward end mounted with a needle, a cooling gas cylinder equipped with a push button and removably mounted at one side of the outer peripheral surface of an intermediate portion between the ends of the cylindrical hollow member, and a cooling-gas injection nozzle member for injecting a cooling gas ejected from the cooling gas cylinder. A forward end of the nozzle member is moved up to a position which is forward or rearward of a forward end of the needle.

4 Claims, 2 Drawing Figures

SYRINGE

BACKGROUND OF THE INVENTION:

1. Field of the invention

The present invention relates to a syringe which permits a fluid to be injected into the body while causing no pain following the piercing of its needle by utilizing the anesthetic effect obtained with the use of a cooling gas.

2. Description of the Prior Art

An attempt has hitherto been made to perform a medical injection while applying in advance a surface anesthetic medicine for example, onto a part of the body from which a syringe needle is to be pierced, so as to mitigate the pain involved as much as possible.

Further, when performing a minor operation for example, sometimes, a cooling gas is applied locally onto the affected or diseased part for purpose of local anesthesia, to thereby anesthetize the same by the cooling action occurring at the time of evaporation.

However, when, as mentioned above, a surface anesthetic is applied to the diseased part to give an injection, the part is not anesthetized to a sufficient extent when it is located at a hard portion such as gums. This requires the injection of an anesthetic medicine by means of a syringe. However, the piercing per se of a syringe needle is followed by a pain, which is counted among the problems occurring with the use of the prior technique.

SUMMARY OF THE INVENTION

The present invention has been achieved in order to solve the problems inherent in the prior art, and its object is to provide a syringe which is equipped, at its portion, with a small-sized cooling gas cylinder, to which an injection nozzle for cooling gas is equipped so that its forward end may be movable between the two positions located forwardly and rearwardly of the forward end of a syringe needle, respectively, by a single-handed operation, thereby enabling both injection of a medicine and application of a cooling gas to be easily, quickly and precisely performed with respect to a desired portion of the body by a doctor's single-handed operation.

The syringe in accordance with the present invention is characterized in that the outer periphery of its cylindrical hollow member mounted with a syringe needle at its forward end is removably fitted, in the vicinity of an intermediate portion between the ends of the member, with a cooling gas cylinder, said gas cylinder being equipped with an injection nozzle member for injecting a cooling gas ejected from the gas cylinder, a forward end of said injection nozzle member being movable between the two positions which are located forwardly and rearwardly of a forward end of the syringe needle, respectively.

When medical injection is desired to be performed with respect to a desired part of the body by using the syringe having the above-mentioned construction, first of all, the injection nozzle member for cooling gas supplied from the cooling gas cylinder is projected up to a position which is immediately forward of the forward end of the medical injection needle. The body of the syringe then is approached to the desired part while it is being held in one hand. Subsequently, a push button of the cooling gas cylinder is depressed with the use of a finger. This causes a cooling gas to be ejected from the injection nozzle member onto the desired part, whereby the part is smoothly and quickly anesthetized. After this cooling anesthetization, the injection nozzle member is retracted from the position in immediate front of the forward end of the syringe needle. The syringe needle whose forward end has now been most forwardly located is then pierced into the anesthetized part. Thereafter, a medicine receptacle is urged toward that part by operating the syringe by a single-handed operation. As a result, the medicine in the receptacle is injected into the diseased part by way of the syringe needle, thus enabling the medical injection to be easily performed with high precision with respect to that diseased part.

DESCRIPTION OF THE PREFERRED EMBODIMENT

An embodiment of the invention will now be described with reference to the appended drawing.

Figure 1:
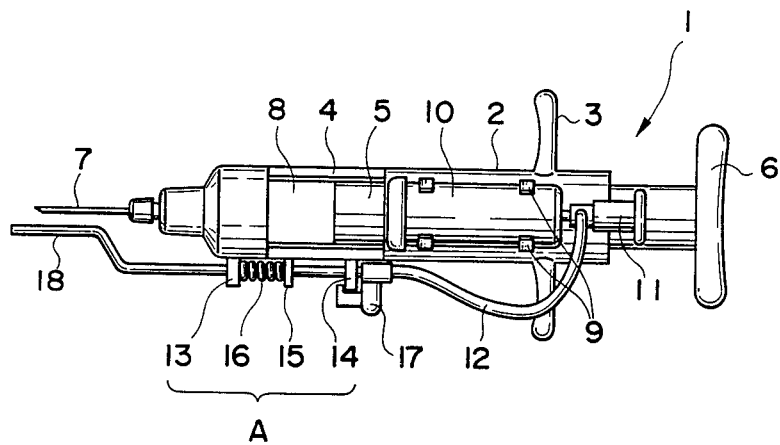
FIG. 1 is a plan view of a dentists' anesthetizing syringe according to the present invention.
Figure 2:
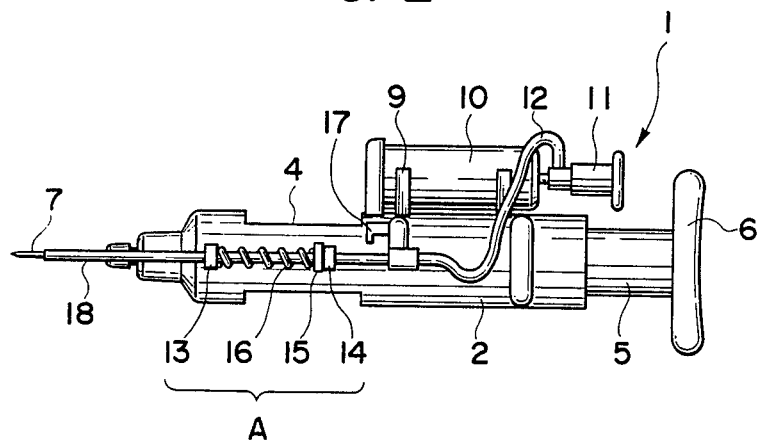
FIG. 2 is a side view thereof.

A syringe according to the invention is constructed as follows. As shown in FIGS. 1 and 2, the syringe 1 comprises a cylindrical hollow member 2 which is removably mounted, at its forward end, with an injection needle 7. The cylindrical hollow member 2 is formed, at the symmetrical outer peripheral portions of an intermediate portion between its ends somewhat nearer to said forward end, with notched windows 4, 4, in such a manner as to resect those outer peripheral portions, said windows 4, 4 permitting a medicine receptacle 8 to be received in the cylindrical hollow member or taken out from the same. Further, into a rear half portion of the cylindrical hollow member 2 there is inserted from a rear end opening thereof a piston 5 integrally formed with a push plate 6, so that the piston 5 may be slidable back and forth by an axial depression of the push plate 6. When medicine injection is performed, the medicine receptacle 8 which has its forward end resected is received from the window 4 or 4 into a portion of the cylindrical hollow member 2 located near the forward end thereof. At this time, it is received so that, when a forwardly pushing force is imparted to the piston 5, the forward end of the medicine receptacle 8 may be pressed against the base end of a syringe needle 7 so as to permit a medicine in the receptacle to be forced into the syringe needle 7.

At opposite positions of an outer-peripheral portion of the rear half portion of the cylindrical hollow member 2 there are projected a pair of finger-engageable portions 3, respectively. At another outer-peripheral portion of the rear half portion of the cylindrical hollow member 2 there are similarly projected from four positions clamping pieces 9 which consist each of a resilient plate member. In the internal area of these clamping pieces 9 there is removably clamped a cooling gas cylinder 10 into a rear end of which a push button 11 is concentrically fitted. This push button 11 is equipped with a continuous gas hose 12 of a specified length.

A supporting elastic unit A the detail of which is shown below is equipped, in an exposed manner, to the outer peripheral surface of a portion of the cylindrical hollow member 2 in the vicinity of the notched windows 4, 4. Firstly, a receiving piece 13 having a bore permitting a nozzle member 18 to be loosely inserted therethrough is projectively formed on the outer-peripheral surface of the forward end portion of the cylindrical hollow member 2 in such a manner as to intersect the longitudinal direction of the member 2 at right angles thereto. Also, an engaging piece 14 of substantially the same shape as the receiving piece 13 is similarly projectively formed on the outer peripheral surface of that portion of the cylindrical hollow member 2 in the vicinity of an intermediate portion between the ends of the notched window 4 which is sapced by a prescribed interval from the position of the receiving piece 13. Between the pieces 13 and 14 there is loosely inserted the rear tube portion of the cooling-gas injection nozzle member 18 which has a specified length and has a supporting piece 15 fitted thereto in the vicinity of its base end, so that the rear tube may pass through the pieces 13 and 14 and be movable back and forth, said rear tube portion thus taking part in the supporting elastic unit A for the nozzle member 18. Further, an urging spring 16 is inserted over that part of the rear tube portion of the nozzle member 18 which resides between the receiving piece 13 and the supporting piece 15.

A base end of the injection nozzle member 18 is connected to a forward end of the above-mentioned gas hose 12. At this connected portion, a hook-like engaging member 17 is fitted onto the outer periphery of the base end of the nozzle member 18. Accordingly, when the hook-like engaging member 17 is engaged with the engaging piece 14 of the supporting elastic unit A in a state wherein the supporting piece 15 is moved against the urging force of the urging spring 16 leftwardly of the illustration, the forward end of the injection nozzle 18 comes to be projected forwards beyond the forward end of the syringe needle 7. Conversely, when the hook-like engaging member 17 having been engaged with the engaging piece 14 is disengaged from this piece 14 by finger operation, the elastic restoring force of the urging spring 16 acts on the supporting piece 15 to cause the same to be retracted up to a position in which it abuts on the engaging piece 14, whereby the forward end of the nozzle member 18 is moved backwards from the forward end of the syringe needle 7. Thus, the members, pieces, spring and elements which are associated with the above operation are incorporated as a whole into a functional unit which constitutes a part of the syringe 1.

In operation, when medicine injection and cooling anesthetization are concurrently performed with respect to a diseased part not shown by using the syringe 1 having the above-mentioned construction, firstly, the medicine receptacle 8 filled with liquid contents is received, from the notched window 4 of the syringe 1, into the corresponding portion of the cylindrical hollow member 2. In this case, the hook-like engaging member 17 which has been fitted over the base end of the injection nozzle member 18 is engaged with the engaging piece 14 located at one end of the supporting elastic unit A, thereby causing the forward end of the nozzle member 18 to be moved forwardly from the forward end of the syringe needle 7. The syringe 1 rearranged in such a manner is held in one hand and then its forward end is approached to the diseased part desired to undergo medicine injection while the syringe is being held in that hand. Thereafter, the push button 11 of the cooling gas cylinder 10 is pushed forwards by a finger of the hand. This pushing operation causes a cooling gas not shown to be ejected from the nozzle member 18 onto the diseased part. As a result, a desired anesthetization of the diseased part is effected smoothly and quickly.

When, after completion of the desired anesthetization, the hook-like engaging member 17 having been engaged with the engaging piece 14 located at one end of the supporting elastic unit A is rotated through a prescribed angle by the tip of a finger of the other hand, it is disengaged from the engaging piece 14. As a result, the forward end of the cooling-gas injection nozzle member 18 is retreated rearwards from that position ahead of the tip end of the medicine-syringe needle 7 in which it has theretofore been located, owing to the restoring force of the urging spring 16. Then, the syringe needle 7 the forward end of which has thus been located most forwardly is pierced into the diseased part not shown which is already anesthetized. Thereafter, the medicine receptacle 8 is urged forwards by the piston 5 by finger operation of the syringe 1 in the hand. This causes the medicine in the receptacle 8 to be injected from the forward end of the syringe needle 7 into the diseased part. Thus, it is possible to easily and precisely perform a desired injection of medicine into the diseased part.

According to the present invention, the cooling gas cylinder equipped with the push button, characteristically, is removably mounted, by being removably clamped, at one side of the outer periphery of an intermediate portion between the ends of the cylindrical hollow member equipped at its forward end with the syringe needle. Further, the cooling gas injection nozzle member at the tip end of the cooling gas cylinder, characteristically, has its forward end moved forwards or rearwards from its position corresponding to the forward end of the syringe needle by engagement or disengagement of the hook-like engaging member fitted on one end of the supporting elastic unit. Thus, since the small-sized cooling gas cylinder is mounted on a part of the cylindrical hollow member, a mere single-handed operation of a medical doctor enables, first, cooling anesthetization of the desired affected part of the body and, then, without any substantial time delay, easy, quick and precise injection of medicine (including anesthetic medicine). This offers an advantage of enabling the performance of a syringe injection which is followed by no pain at the time of piercing the syringe needle.

The invention is not limited to the above-mentioned embodiment but permits suitable changes or modifications to be made of the configuration of the syringe, the installation position of the cooling gas cylinder, etc. without departing from the spirit and scope of the invention.

What is claimed is:
1. A painless injection device, comprising:
   a syringe portion including a cylindrical hollow member, needle disposed at a first end of said hollow member for penetrating tissue to be injected and plunger means for forcing liquid from said hollow member through said needle means;
   means mounted on said syringe portion for storing a cooling gas;
   nozzle means for applying cooling gas from said storing means to the tissue to be injected, for anesthetizing the tissue; and
   means for advancing and retracting said nozzle means relative to said needle means, whereby said nozzle means may be positioned closer to the tissue than said needle means during anesthetizing and retracted during injection so as to allow the operator a clear view of the tissue during injection.

2. Apparatus according to claim 1, wherein said storing means includes for controlling the flow of said cooling gas to said nozzle means.

3. Apparatus according to claim 1, wherein said advancing and retracting means comprises:
   means for biasing said nozzle means to a retracted position relative to said needle means;
   a hook-like engaging member on said cylindrical hollow member; and
   an engaging means on said nozzle means for engaging said engaging member when said nozzle member is in an advanced position, whereby said nozzle member automatically returns to a retracted position when said engaging means is disengaged from said engaging member.

4. A method of painlessly injecting tissue with an apparatus including a syringe portion having a needle, means mounted on the syringe portion for storing a cooling gas, nozzle means for applying the cooling gas to the tissue to be injected and means for advancing and retracting the nozzle means, the method comprising:
   (a) advancing the nozzle means in a first direction to extend beyond the syringe portion;
   (b) applying cooling gas from the storing means through the nozzle to the tissue to anesthetize the tissue;
   (c) retracting the nozzle member so that the syringe needle extends the nozzle member in the first direction; and
   (d) injecting the anesthetized tissue with the syringe.

* * * * *